US006521595B1

(12) United States Patent
Kim et al.

(10) Patent No.: US 6,521,595 B1
(45) Date of Patent: Feb. 18, 2003

(54) NONIMMUNOSUPPRESSIVE [γ-HYDROXY-METHYLLEUCINE⁴] CYCLOSPORIN A, HAIR GROWTH STIMULATOR AND EXTERNAL COMPOSITION FOR SKIN USING THE SAME

(75) Inventors: Sang-Nyun Kim, Kaejeon (KR); Ho-Jeong Ahn, Daejeon (KR); Myung-Kee Kim, Daejeon (KR); Jong-Il Kim, Daejeon (KR); Jung-Hun Kim, Daejeon (KR); Chang-Woo Lee, Daejeon (KR); Min-Ho Lee, Daejeon (KR); Chang-Deok Kim, Daejeon (KR); Ho-Song Cho, Daejeon (KR); Hyun-Sik Kim, Daejeon (KR); Min-Hwan Jung, Daejeon (KR); Seung-Jin Kim, Seoul (KR)

(73) Assignee: LG Chemical, Ltd., Seoul (KR)

( * ) Notice: Subject to any disclaimer, the term of this patent is extended or adjusted under 35 U.S.C. 154(b) by 0 days.

(21) Appl. No.: 09/580,694

(22) Filed: May 30, 2000

(30) Foreign Application Priority Data

Nov. 19, 1999 (KR) ............................................. 99-51646
Mar. 23, 2000 (KR) ............................................. 00-14837

(51) Int. Cl.⁷ ......................... A61K 38/13; A61K 38/12; A61K 38/00; A01J 21/00
(52) U.S. Cl. .................. 514/11; 514/2; 514/9; 514/828; 514/880; 514/881; 530/317; 530/318; 530/322; 424/401; 424/78.03
(58) Field of Search .............................. 424/401, 78.03; 530/317, 318, 322; 514/2, 9, 11, 828, 880, 881

(56) References Cited

U.S. PATENT DOCUMENTS 5,767,069 A * 6/1998 Ko et al. ........................ 514/11
5,807,820 A * 9/1998 Elias ............................ 514/11

* cited by examiner

Primary Examiner—Christopher S. F. Low
Assistant Examiner—Abdel A. Mohamed
(74) Attorney, Agent, or Firm—Alston & Bird LLP

(57) ABSTRACT

The present invention relates to methods for treating alopecia and stimulating hair growth and pharmaceutical compositions using nonimmunosuppressive [γ-hydroxy-methylleucine⁴] cyclosporin A having superior hair growth-promoting effect, wherein the hydroxyl group is added to the carbon position of No. 4 methylleucine of cyclosporin A by the microorganism.

2 Claims, 18 Drawing Sheets

FIG.7

| Fragment | 1 | 2 | 3 | 4 | 5 | 6 | 7 | 8 | 9 | 10 | 11 | m/z[Cs A] | m/z[Cs A metabolite] |
|---|---|---|---|---|---|---|---|---|---|---|---|---|---|
| [M+H]+ | o | o | o | o | o | o | o | o | o | o | o | 1202.4 | 1218.5 |
| $b^{1-11}_{10}$ | o | o | o | o | o | o | o | o | o | o |  | 1089.6 | 1105.5 |
| $b^{1-11}_{9}$ | o | o | o | o | o | o | o | o | o |  |  | 962.5 | 978.4 |
| $b^{1-11}_{8}$ | o | o | o | o | o | o | o | o |  |  |  | 835.4 | 851.3 |
| $b^{1-11}_{6}$ | o | o | o | o | o | o |  |  |  |  |  | 693.3 | 709.3 |
| $b^{2-3}_{9}$ |  |  | o | o | o | o | o | o | o | o | o | 934.3 | 950.3 |
| $b^{2-3}_{8}$ |  |  | o | o | o | o | o | o | o | o |  | 821.3 | 837.3 |
| $b^{2-3}_{7}$ |  |  | o | o | o | o | o | o | o |  |  | 694.3 | 710.3 |
| $b^{2-3}_{6}$ |  |  | o | o | o | o | o | o |  |  |  | 567.2 | 583.2 |
| $b^{2-3}_{4}$ |  |  | o | o | o | o |  |  |  |  |  | 425.1 | 441.1 |
| $b^{2-3}_{3}$ |  |  | o | o | o |  |  |  |  |  |  | 298.1 | 314.1 |
| $b^{2-3}_{2}$ |  |  | o | o |  |  |  |  |  |  |  | 198.9 | 214.9 |
| $b^{5-6}_{6}$ |  |  |  |  |  | o | o | o | o | o | o | 637.3 | 637.2 |
| $b^{5-6}_{5}$ |  |  |  |  |  | o | o | o | o | o |  | 524.2 | 524.2 |
| $b^{5-6}_{4}$ |  |  |  |  |  | o | o | o | o |  |  | 397.1 | 397.1 |
| $b^{1-11}_{10}-18$ | o | o | o | o | o | o | o | o | o | o |  | 1071.4 | 1087.5 |
| $b^{1-11}_{9}-18$ | o | o | o | o | o | o | o | o | o |  |  | 944.3 | 961.2 |
| $b^{1-11}_{6}-18$ | o | o | o | o | o | o |  |  |  |  |  | 675.3 | 691.2 |
| $b^{1-11}_{5}-18$ | o | o | o | o | o |  |  |  |  |  |  | 548.3 | 564.1 |
| $b^{1-11}_{4}-18$ | o | o | o | o |  |  |  |  |  |  |  | 449.1 | 465.2 |
| $b^{1-11}_{3}-18$ | o | o | o |  |  |  |  |  |  |  |  | 322 | 322 |

Cyclosporine A SRD.

DEFT 90

DEFT 135

Normal C

CsA spectra

NONIMMUNOSUPPRESSIVE [γ-HYDROXY-METHYLLEUCINE⁴] CYCLOSPORIN A, HAIR GROWTH STIMULATOR AND EXTERNAL COMPOSITION FOR SKIN USING THE SAME

CROSS REFERENCE TO RELATED APPLICATION

This application is based on application Nos. 10-1999-0051646 and 10-2000-0014837 filed in the Korean Industrial Property Office on Nov. 19, 1999 and Mar. 23, 2000 respectively, the contents of which are incorporated hereinto by reference.

BACKGROUND OF THE INVENTION (a) Field of the Invention

The present invention relates to methods and pharmaceutical compositions for treating alopecia and promoting hair growth using nonimmunosuppressive [γ-hydroxymethylleucine⁴] cyclosporin A.

(b) Description of the Related Art

Approximately 100,000 to 150,000 hairs exist on a human body, each hair growing and falling out through the different cycles of anagen, catagen, and telogen. These cycles are repeated every 3 to 6 years resulting in a normal loss of 50 to 100 hairs per day, on average. Alopecia generally means that the proportion of hairs in the anagen cycle is decreased, and the proportion of hairs in the telogen or catagen cycles is increased, so many hairs abnormally fall out. These situations include male pattern alopecia, alopecia senilis, alopecia areata etc.

Factors such as poor blood circulation toward hair follicle, excessive male sex hormone, seborrhea, scalp function deterioration due to peroxides, bacteria, etc., hereditary factors, aging, and stress are often given as reasons for the alopecia, but explicit reasons have not been identified thus far.

A preparation containing minoxidil, which is the most widely used medication thus far in the treatment or prevention of alopecia, is one of two hair-restorers which have received U.S. Food and Drug Administration authorization so far. Even though minoxidil was developed as a medication for reducing blood pressure, it is now more famous as a hair-restorer because of the trichological activity that occurs owing to its side effects. Although the hair growth-stimulating mechanisms of minoxidil have not yet been fully discovered, blood flow increase through vasodilatation effects is thought to be supplying nutrition to the hair roots, thus promoting hair growth. This blood flow increase model is indirectly validated by the recent report that minoxidil increases the expression of VEGF (vascular endothelial growth factor), a growth factor related to vasodilatation, at the dermal papilla which is a major cell forming the hair root (Br. J. of Dermatol., 1998; 138; 407–411). Furthermore, dermal papilla cell activation of hair roots (Skin Pharmacol., 1996; 9; 3–8), and studies showing that hair follicle growth is promoted in the hair follicle tissue culture (e.g. J. Invest. Dermatol., 1989; 92; 315–320), in addition to the vasodilatation effects in the hair growth-stimulating effect mechanisms of minoxidil, suggest that minoxidil can act as a direct growth factor.

Additionally, the Merck Corporation's recently commercially available Propecia, principal ingredient being finasteride, inhibits the transformation of male sex hormone testosterone into dehydrotestosterone, a more potent male sex hormone. Although it became clear that finasteride showed notable effects on male pattern, side effects of partial suppression for male sex function have been reported (J. Am. Acad. Dermatol., 1998; 39; 578–589).

It has been reported that cyclosporin is not only a representative immunosuppressant, but it also brings about various physiological effects such as nephrotoxicity, hepatotoxicity, high blood pressure, hair growth-stimulating effect, gingival over growth, and antimicrobial effects against for viruses, fungi, and protozoa (Advances in Pharmacol., 1996; 35; 114–246 and Drug Safety, 1994; 10;310–317). A representive cyclosporin A is shown in the following Structural Formula 1 as a cyclic peptide with 11 amino acids comprising various N-methyl amino acids, and D-alanine at the No. 8 position.

[Structural Formula 1]

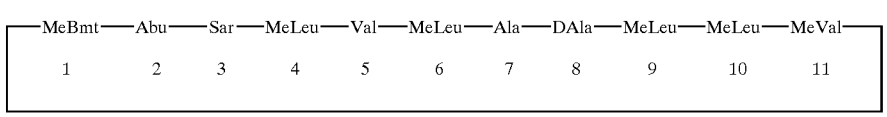

where MeBmt is N-methyl-(4R)-4-[(E)-2-butenyl]-4-methyl-L-threonine; Abu is L-aminobutyric acid; Sar is sarcosine; MeLeu is N-methyl-L-leucine; Val is L-valine; Ala is L-alanine; DAla is D-alanine; and MeVal is N-methyl-L-valine. Amino acid form of the above cyclosporin A has a L-configuration, unless otherwise specified.

Possibilities for the development of cyclosporin as a new hair growth stimulator using excessive hair growth side effects have been reviewed in a variety of studies. Among them, animal hair growth-stimulating tests (Arch, Dermatol. Res., 1996; 288; 408–410), human alopecia areata (J. Am. Acad. Dermatol., 1990; 22; 242–250), human male pattern alopecia (J. Am. Acad. Dermatol., 1990; 22; 251–253 and Skin Pharmacol., 1994; 7; 101–104), and protection from chemotherapy-induced alopecia (Clin. Lab. Invest., 1995; 190; 192–196 and J. Pathol., 1997: 150; 1433–1441) have been reported.

Several patents disclosed the use of cyclosporins and related derivatives for hair revitalization (Japanese Laid-open Patent Publication Nos. Showa 60-243008, Showa 62-19512, and Showa 62-19513, a cyclosporin derivative with the No. 8 position changed in European Laid-open Patent Publication No. 0414632B1, and isocyclosporin in World Laid-open Patent Publication No. 93/17039). In addition, U.S. Pat. No. 5,807,820 and U.K. Patent No. 2,218,334A disclose an enhanced transdermal absorption of cyclosporin for the use of cyclosporin as a treatment of alopecia. However, the serious immunosuppressive side effects associated with cyclosporin A do not justify its general use for trichological purposes. Accordingly, there is need for nonimmunosuppressive cyclosporin derivatives useful as hair revitalizing compounds.

In view of the forgoing problem in the prior art, an object of the present invention is to provide nonimmunosuppressive cyclosporin A derivatives of which the hair growth-stimulating effects are maintained while a degree of immunosuppression is lost, through various molecular changes of cyclosporin molecule, on the basis of the current discoveries that the hair growth-stimulating effects do not necessarily correlate with the immunosuppressive activity of cyclosporin molecules (Iwabuchi et al., J. Dermatol. Sci., 1995; 9; 64–69).

As an approach similar to this, studies on derivatives in which suppression of the human immunodeficiency virus (HIV) is maintained while a degree of immunosuppression is decreased are actively being pursued, particularly with derivatives in which the MeLeu group at the position 4 is replaced by a variety of N-methylated amino acid, for example γ-hydroxy-methylleucine, methylisoleucine, methylvaline, methylthreonine, methylalanine, which have been reported in patents (European Patent No. 484281 A2, U.S. Pat. Nos. 5,767,069, 5,981,479) and literature (J. Virol., 1995; 69: 2451–2461, J. Antibiotics, 1996; 49: 781–787) as new anti-HIV preparations.

As a result of studies of the inventors for attaining the nonimmunosuppressive cyclosporine derivatives for a new hair growth stimulator, it has now been found that [γ-hydroxy-methylleucine⁴] cyclosporin A is the only one in which a degree of immunosuppression is lost while the hair growth stimulating effect is uniquely maintained among various derivatives including a derivative in which the original No. 4 amino acid, methylleucine, is substituted with the similarly structured γ-hydroxy-methylleucine, methylisoleucine, methylvaline, methylalanine, leucine, or isoleucine and [Des-MeLeu⁴]-cyclosporin A, [Des-MeLeu⁴, Des-Val⁵]-cyclosporin A, and others, thereby accomplishing the present invention.

SUMMARY OF THE INVENTION

The present invention provides the methods and pharmaceutical compositions for treating alopecia and promoting hair growth using nonimmunosuppressive [γ-hydroxy-methylleucine⁴] cyclosporin A, which is excellent in hair growth and hair loss protecting effect on human hair, represented as in the following Chemical Formula 1, in which the hydroxyl group is added to the carbon position of No. 4 methylleucine of cyclosporin A by a microbial metabolic procedure. "Treating alopecia and promoting hair growth" refers to maintaining, inducing, stimulating, accelerating, or revitalizing the germination of hair.

moting hair growth on the skin of mammals and, in particular, on human skin.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein:

FIG. 7 is a table in which the Collision Induced Dissociation results of cyclosporin A and [γ-hydroxy-methylleucine⁴] cyclosporin A are compared using the fragment ion mass spectrum;

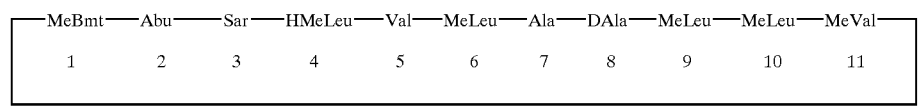

[Chemical Formula 1]

where MeBmt is N-methyl-(4R)-4-[(E)-2-butenyl]-4-methyl-L-threonine; Abu is L-aminobutyric acid; Sar is Sarcosine; HMeLeu is γ-hydroxy-methylleucine; Val is L-valine; MeLeu is N-methyl-L-leucine; Ala is L-alanine; DAla is D-alanine; and MeVal is N-methyl-L-Valine.

Figure 12:
Figure 12:
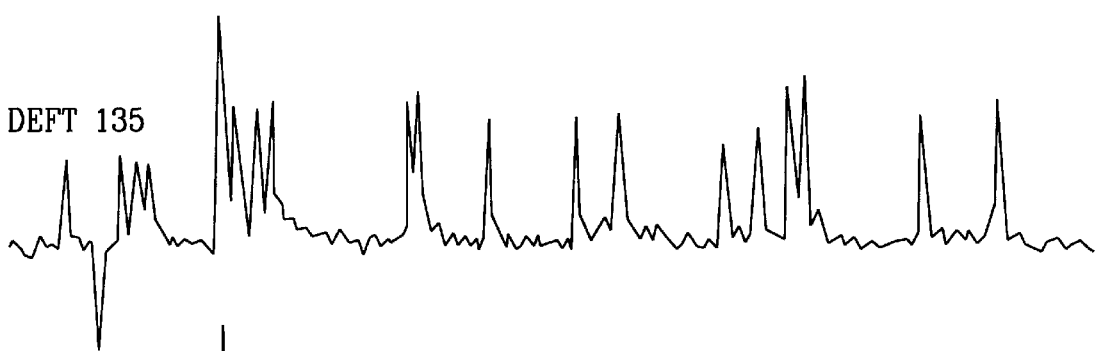
Figure 12:
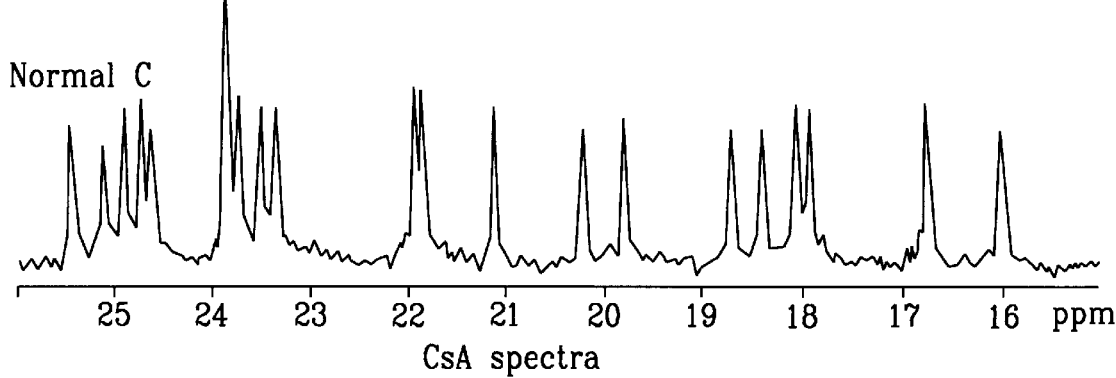
Figure 13:
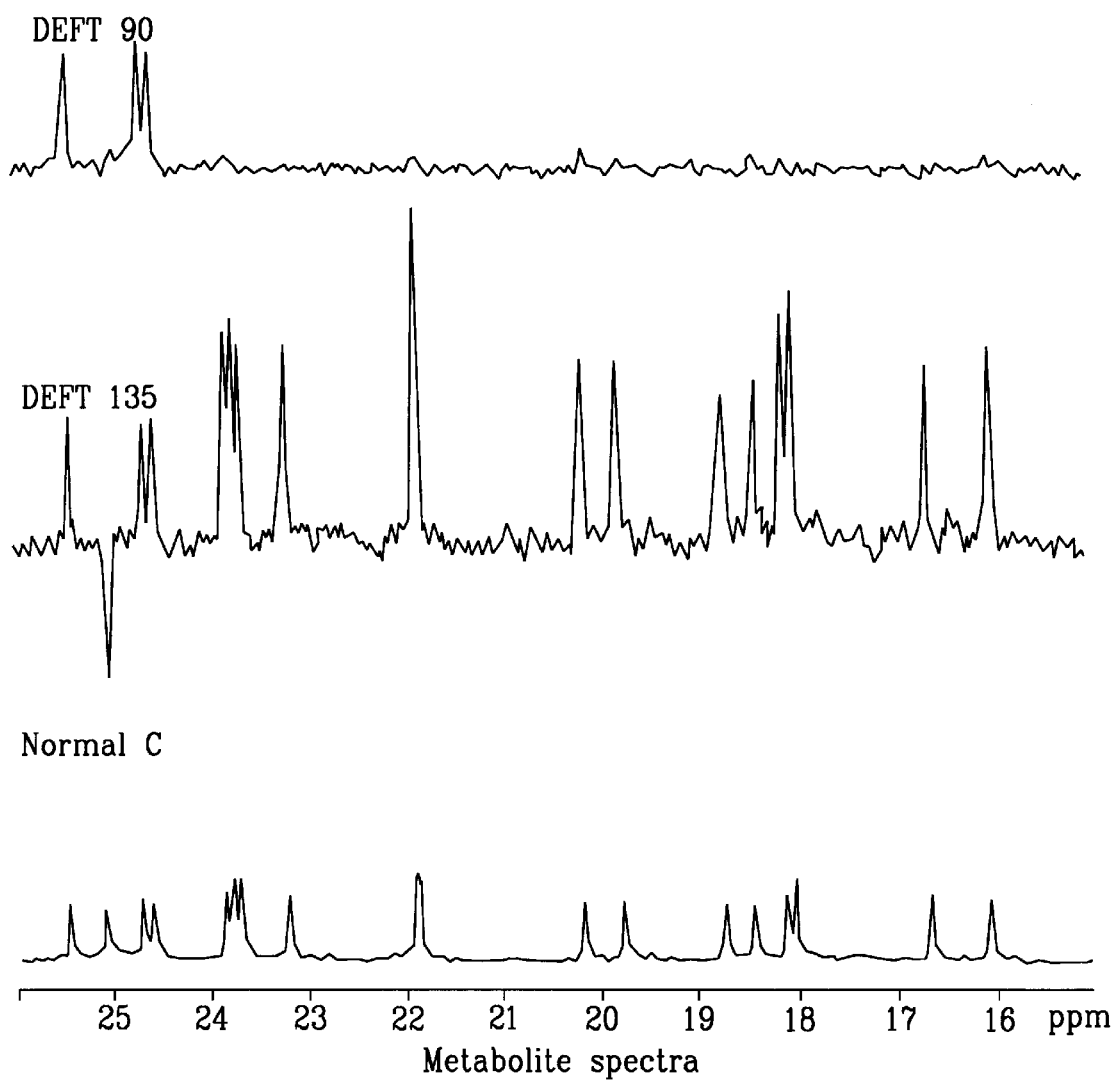
Figure 14:
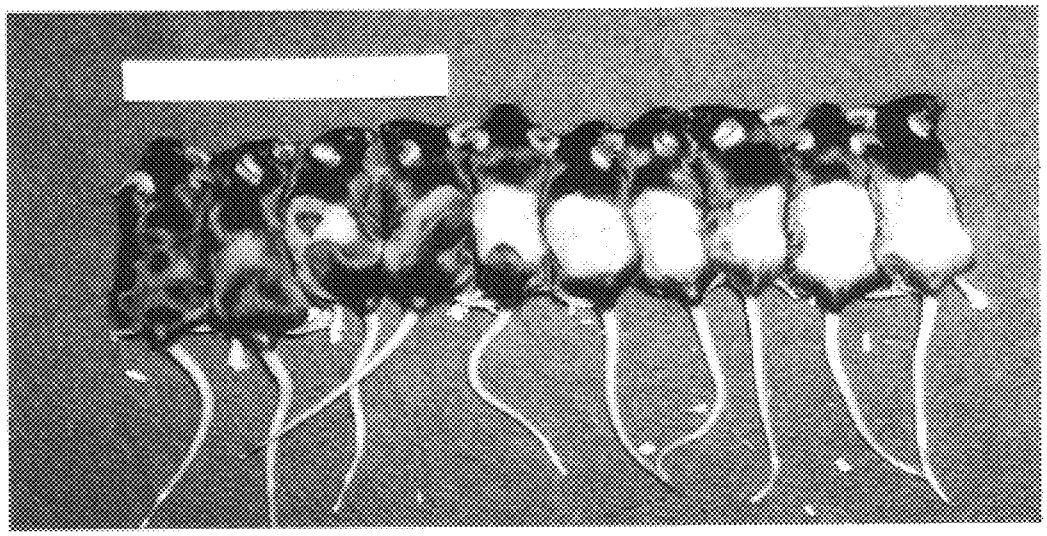
Figure 15:
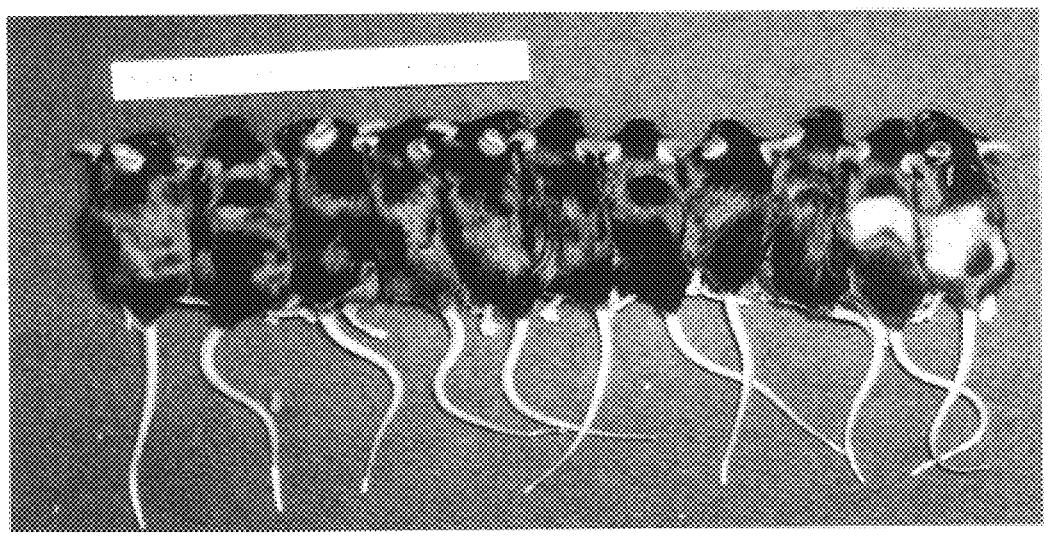
Figure 16:
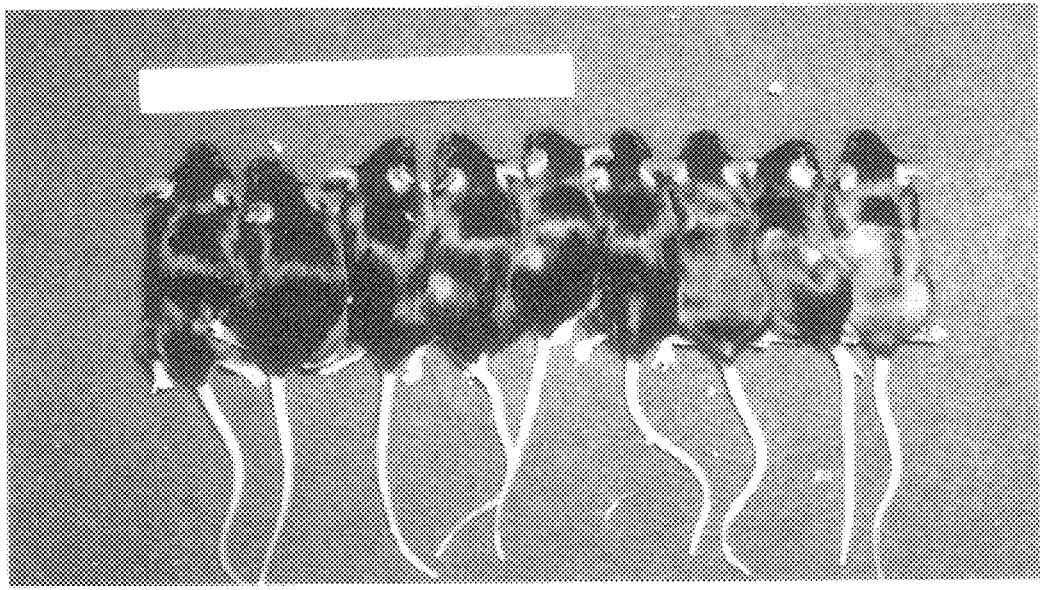
Figure 17:
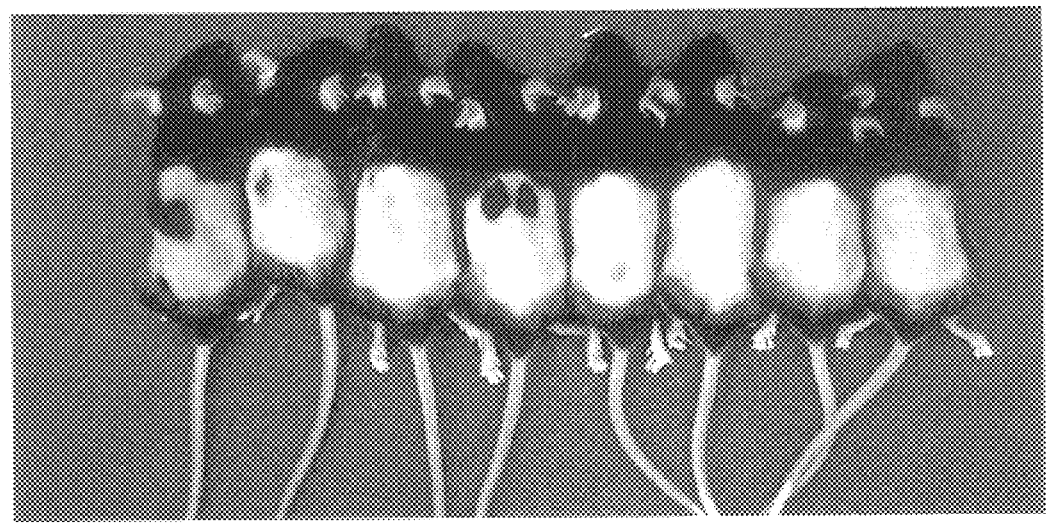
Figure 18:
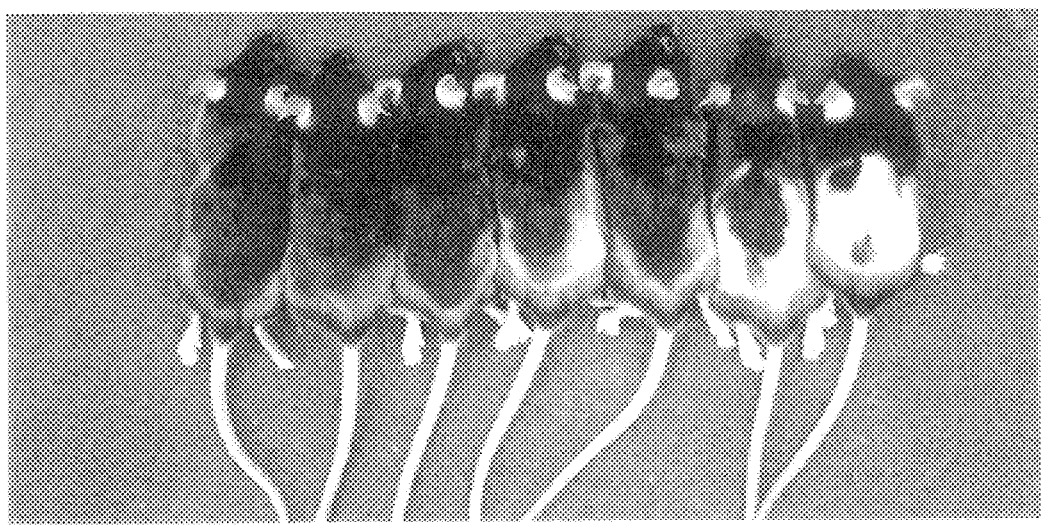
Figure 19:
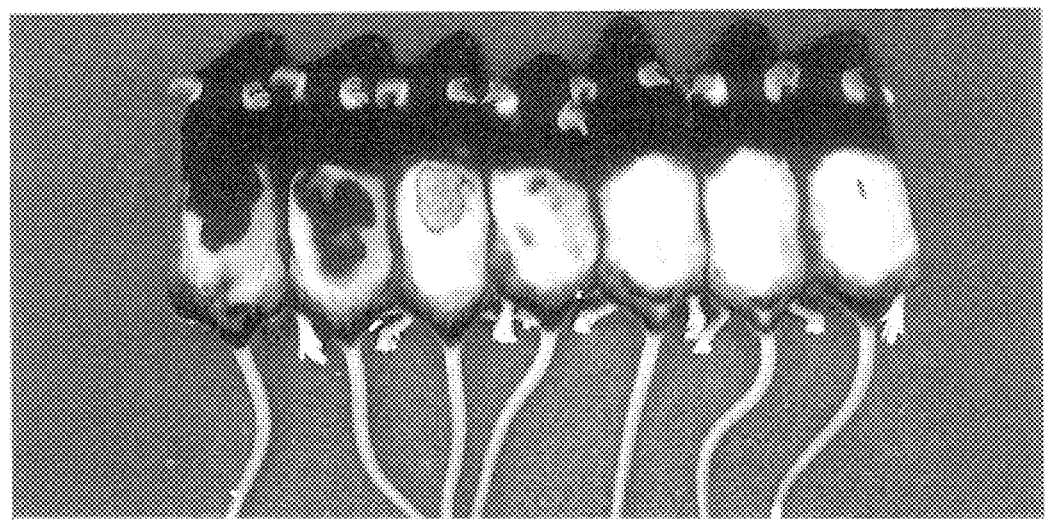
Figure 20:
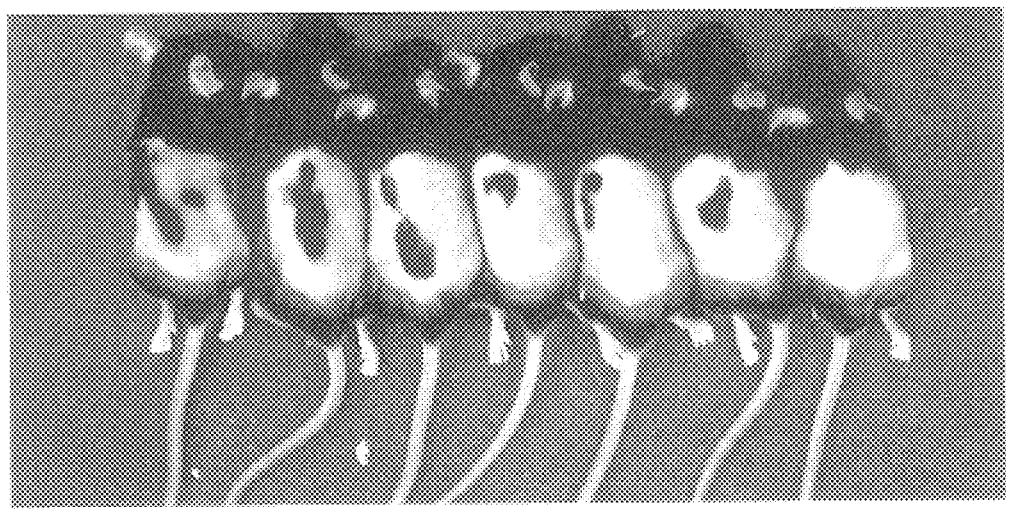
Figure 21:
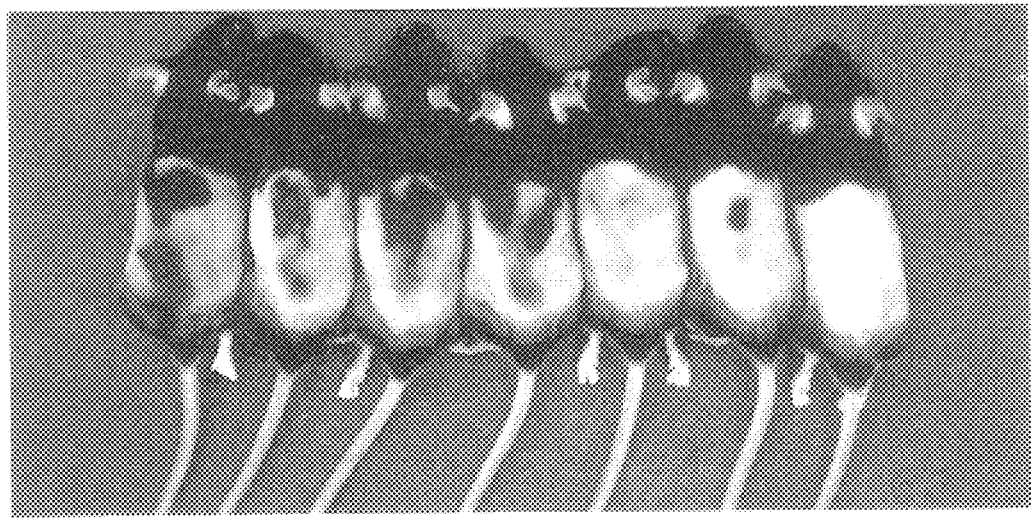
Figure 22:
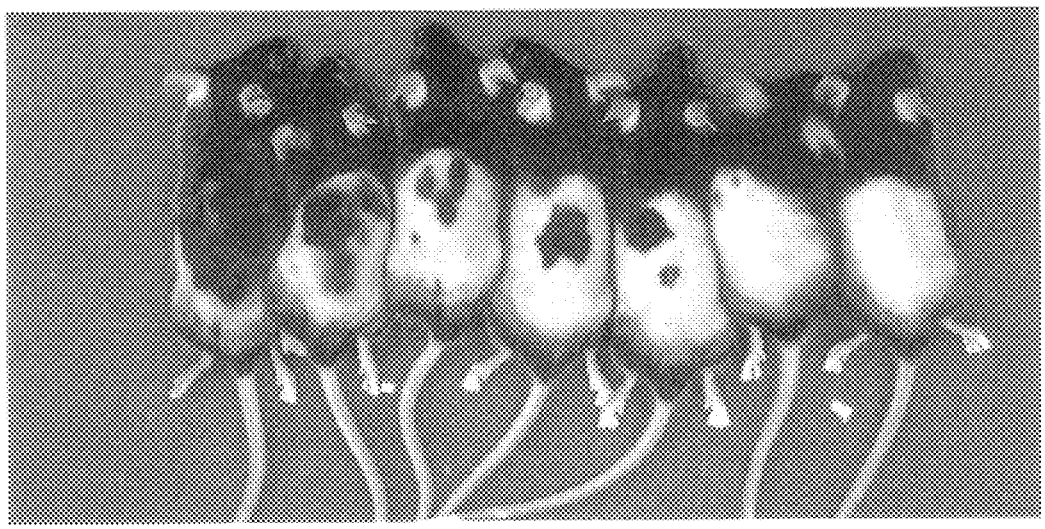

Furthermore, the present invention provides pharmaceutical compositions in the form of a liquid phase, a spray, gel, paste, emulsion, cream, conditioner, or shampoo which comprises an effective amount of [γ-hydroxy-methylleucine⁴] cyclosporin A for treating alopecia or pro- FIG. 12 illustrates the DEPT (distortionless enhancement by polarization transfer) result on the vicinity of the peak disappeared in the cyclosporin A molecules after the conversion, showing that the 4 peaks represent methine carbons in 4 methylleucines of cyclosporin A;

FIG. 13 illustrates the DEPT (distortionless enhancement by polarization transfer) results of [γ-hydroxy-methylleucine⁴] cyclosporin A molecules showing that the peak disappeared is a methine carbon in a methylleucine;

FIGS. 14–16 show photographs for the comparision of nonimmunosuppressive [γ-hydroxy-methylleucine⁴] cyclosporin A to immunosuppressive cyclosporin A, with respect to their hair revitalizing effects;

FIG. 14 is a photograph of C57BL/6 mice treated with a vehicle;

FIG. 15 shows the remarkable ability of the nonimmunosuppressive [γ-hydroxy-methylleucine⁴] cyclosporin to achieve hair regrowth, wherein the hair revitalizing effect is similar to cyclosporin A-treated mice shown in FIG. 16;

FIG. 16 is a photograph of C57BL/6 mice treated with cyclosporin A, showing the remarkable hair growth on mice;

FIG. 17–FIG. 23 show photographs for hair growth-stimulating effects of cyclosporin A, [MeIle⁴] cyclosporin A, [MeVal⁴] cyclosporin A, [MeAla⁴] cyclosporin A, [Leu⁴] cyclosporin A, and [Ile⁴] cyclosporin A on C57BL/6 mice;

FIG. 17 is a photograph of C57BL/6 mice treated with a vehicle;

FIG. 18 is a photograph of C57BL/6 mice treated with cyclosporin A, showing the remarkable hair growth on mice;

FIG. 19 is a photograph of C57BL/6 mice treated with [MeIle⁴] cyclosporin A;

FIG. 20 is a photograph of C57BL/6 mice treated with [MeVal⁴] cyclosporin A;

FIG. 21; is a photograph of C57BL/6 mice treated with [Leu⁴] cyclosporin A cyclosporin;

FIG. 22 is a photograph of C57BL/6 mice treated with [Ile⁴] cyclosporin A; and

Figure 23:
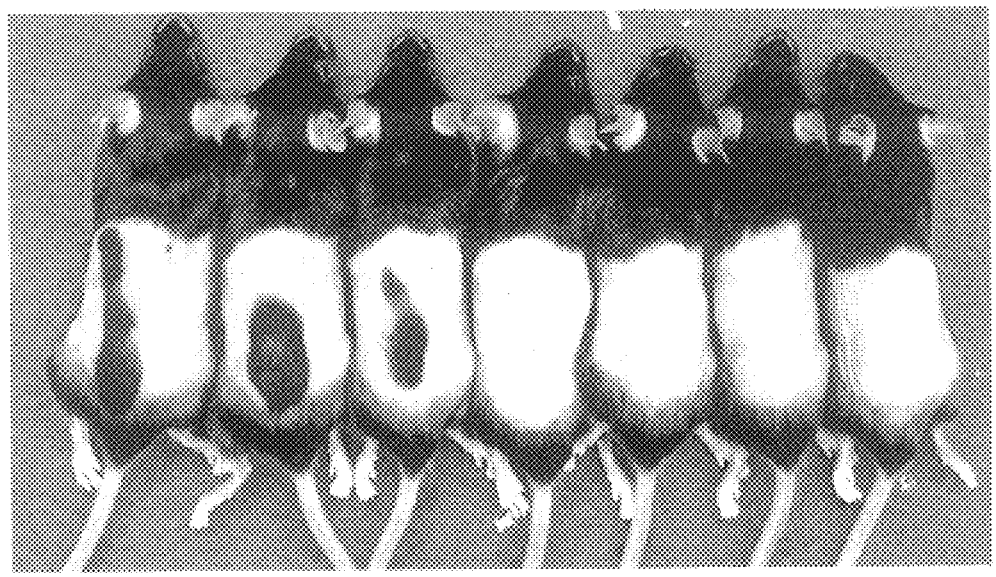

FIG. 23 is a photograph of C57BL/6 mice treated with [MeAla⁴] cyclosporin A.

DETAILED DESCRIPTION OF THE PREFERRED EMBODIMENTS

In the following detailed description, only the preferred embodiments of the invention have been shown and described, simply by way of illustration of the best mode contemplated by the inventor(s) of carrying out the invention. As will be realized, the invention is capable of modification in various obvious respects, all without departing from the invention. Accordingly, the description is to be regarded as illustrative in nature, and not restrictive.

The present invention is described in detail as following:

Alopecia referring to deficient hair growth and loss of hair, occurs in a variety of situations such as androgenic alopecia (male pattern baldness), alopecia senilis, alopecia areata, and others. As a result of studies for attaining the nonimmunosuppressive cyclosporine derivatives for a new hair growth stimulator, it has now been discovered that [γ-hydroxy-methylleucine⁴] cyclosporin A is the only one in which a degree of immunosuppression is lost while hair growth stimulating effect is uniquely maintained among various derivatives of the following REFERENCE EXAMPLES and EXAMPLE 1 including derivatives in which the original No. 4 amino acid, methylleucine, is substituted with the similarly structured γ-hydroxy-methylleucine, methylisoleucine, methylvaline, methylalanine, leucine, or isoleucine and [Des-MeLeu⁴]-cyclosporin A, [Des-MeLeu⁴, Des-Val⁵]-cyclosporin A, and others.

REFERENCE EXAMPLES

Reference Example 1
Preparation of [methylisoleucine⁴] cyclosporin A

For the preparation of the title compound, a general route was devised. It consisted of utilising the decapeptide H-Val-MeLeu-Ala-(D)Ala-MeLeu-MeLeu-MeVal-MeBmt(OAc)-Abu-Sar-OMe as open cyclosporin precursor, coupling it with Boc-MeIle-OH using benzotriazole-1-yl-oxy-tris-(dimethylamino)-phosphonium hexafluorophosphate and removing the protecting groups with sodium hydroxide (NaOH) and trifluoroacetic acid(TFA), cyclising the resulting undecapeptide, after deprotection of acetyl group using sodium methoxide(NaOMe), to afford the title compound.

Reference Example 2
Preparation of [MeVal⁴] cyclosporin A

[MeVal⁴] cyclosporin A was synthesized by a procedure analogues to the REFERENCE EXAMPLE 1 except that Boc-MeVal-OH was used instead of Boc-MeIle-OH.

Reference Example 3
Preparation of [Leu⁴] cyclosporin A

[Leu⁴] cyclosporin A was synthesized by a procedure analogues to the REFERENCE EXAMPLE 1 except that Boc-Leu-OH was used instead of Boc-MeIle-OH.

Reference Example 4
Preparation of [Ile⁴] cyclosporin A

[Ile⁴] cyclosporin A was synthesized by a procedure analogues to the REFERENCE EXAMPLE 1 except that Boc-Ile-OH was used instead of Boc-MeIle-OH.

Reference Example 5
Preparation of [MeAla⁴] cyclosporin A

[MeAla⁴] cyclosporin A was synthesized by a procedure analogues to the REFERENCE EXAMPLE 1 except that Boc-MeAla-OH was used instead of Boc-MeIle-OH.

Reference Example 6
Preparation of cyclosporin A-acetate

To a stirred solution of 3.6 g (30 mmol) of cyclosporin A in 100 ml tetrahydrofuran were added 1.5 equivalents of acetic anhydride, 1.5 equivalents of triethylamine, and 0.3 g of dimethylaminopyridine. The mixture was refluxed for 18 hours. The solvent was evaporated under reduced pressure and the residue was dissolved in ethyl acetate, washed sequentially with 1N hydrochloric acid solution, water, dried over $MgSO_4$ and evaporated. The crude product was chromatographed to give a title compound of 3.2 g.

Reference Example 7
Preparation of seco-cyclosporin undecapeptide (H-MeLeu-Val-MeLeu-Ala-D-Ala-MeLeu-MeLeu-MeVal-MeBmt(OAc)-Abu-Sar-OMe)

To a stirred solution of 3.2 g of cyclosporin A-acetate in 30 ml dichloromethane was added 2.5 equivalents of trimethyloxonium tetrafluoroborate $((CH_3)_3O^+BF_4^-)$. The mixture was kept at the room temperature for 20 hours. After adding 1.2 equivalents of sodium methoxide dissolved in methanol to the mixture, it was stirred for 30 minutes. After putting 10 ml of 1 M sulfuric acid solution and 10 ml of methanol into it, the mixture was acid hydrolyzed for 15 minutes. The solvent was evaporated under reduced pressure and the crude product was chromatographed to give a seco-cyclosporin undecapeptide of 2.0 g (Wenger, The European Peptide Society, 1998; 173–177).

Reference Example 8
Preparation of [Des-MeLeu⁴]-cyclosporin A-acetate

After removing methylleucine from the above seco-cyclosporin undecapeptide by the Edman method (Eur. J. Biochem., 1967; 1; 80), [Des-MeLeu⁴] cyclosporin A-acetate was obtained by the cyclization.

Reference Example 9
Preparation of [Des-MeLeu⁴]-cyclosporin A

After adding sodium methoxide (NaOCH₃) dissolved in methanol to [Des-MeLeu⁴]-cyclosporin A-acetate, it was stirred for 3 hours. Then the solution was acidified with acetic acid. The solvent was evaporated under reduced pressure and the residue was dissolved in ethyl acetate, washed sequentially with water, brine, and NaHCO₃ solution, dried over MgSO₄ and evaporated. The crude product was chromatogrphed to give a [Des-MeLeu⁴]-cyclosporin A.

Reference Example 10
Preparation of [Des-MeLeu⁴, Des-Val⁵]-cyclosporin A-acetate

[Des-MeLeu⁴, Des-Val⁵] cyclosporin A-acetate was obtained by the same synthesizing method as [Des-MeLeu⁴] cyclosporin A.

Reference Example 11
Preparation of [Xaa¹]-cyclosporin A 6 types of heptapeptide (H-Xaa-Abu-Sar-MeLeu-Val-MeLeu-Ala-Obzl) substituted with other amino acids instead of MeBmt were 4+7 fragment condensed with the tetrapeptide (Fmoc-D-Ala-MeLeu-MeLeu-MeVal-OH) with aid of the reagent of BOP. The C-terminal benzyl group and N-terminal Fmoc-group were removed and the unprotected undecapeptide was cyclized using propylphosphonic anhydride and 4-(dimethyl amino)pyridine. This reaction was represented in the following Reaction Formula 1:

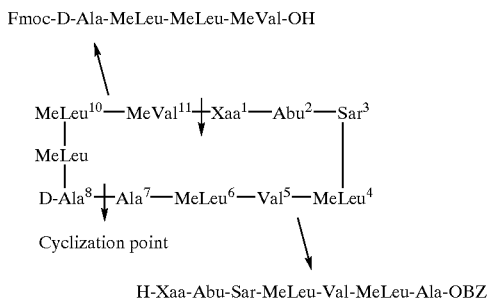

where Xaa¹, a substituted amino acid, is Leu, Phe, MeLeu, Gly, Ala, or MeVal.

The present invention is described more in detail through the following EXAMPLES and TEST EXAMPLES. However, EXAMPLES are only for exemplifying the present invention, and the present invention is not limited to the EXAMPLES.

Example 1
Preparation of [γ-hydroxy-methylleucine⁴] cyclosporin A

The preparation of [γ-hydroxy-methylleucine⁴] cyclosporin A in which hair growth-stimulating effects are maintained while a degree of immuno-suppression is lost is described here.

The [γ-hydroxy-methylleucine⁴] cyclosporin A is obtained from biotransformation of cyclosporin A by the Sebekia benihana KCTC 9173 which is able to hydroxylate novobiocin. The composition of the culture for the biotransformmation is as follows: glucose 0.7%, yeast extract 0.45%, malt extract 0.5%, soluble starch 1.0%, and calcium carbonate (CaCO₃) 0.005% (J. Antibiotics, 1996; 49; 781–787).

Figure 1:
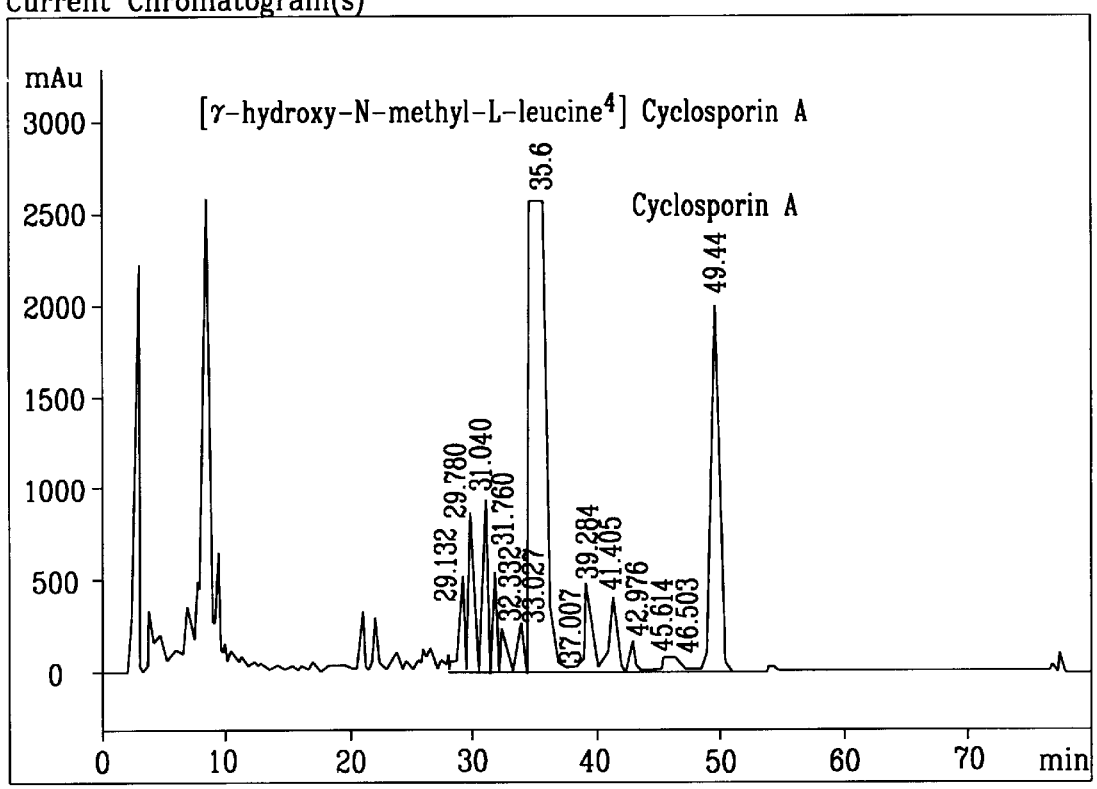
FIG. 1 is the liquid chromatography result for a cyclosporin A and [γ-hydroxy-methylleucine⁴] cyclosporin A, a biotransformed derivative by microorganisms.
Figure 2:
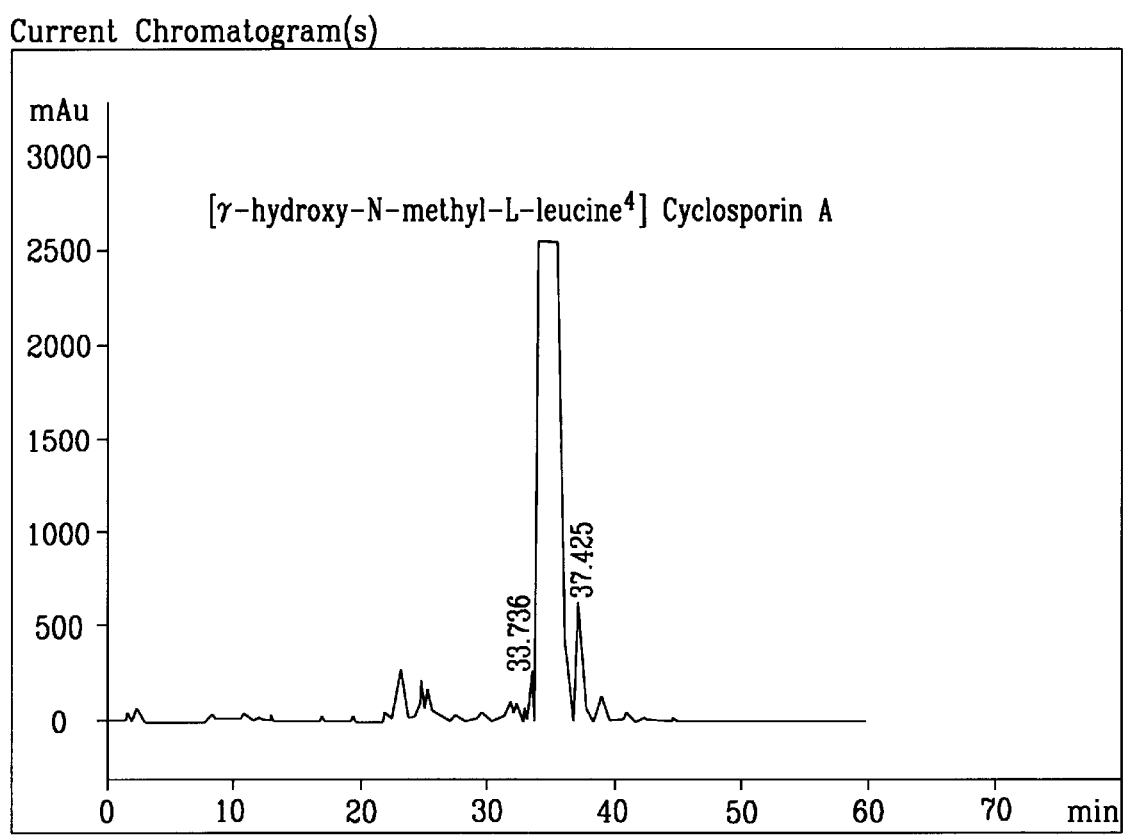
FIG. 2 is the liquid chromatography result obtained by injection of the purified [γ-hydroxy-methylleucine⁴] cyclosporin A.
Figure 3:
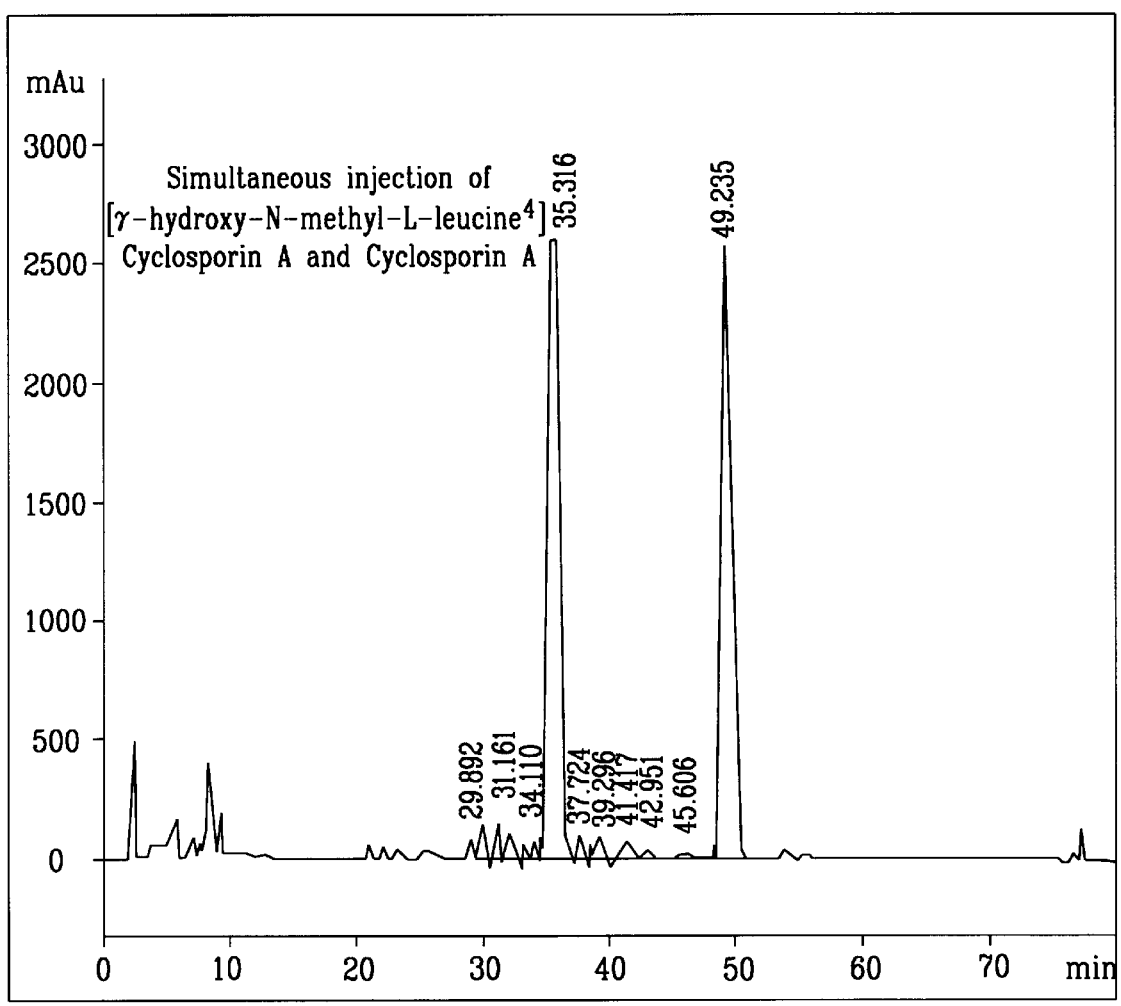
FIG. 3 is the liquid chromatography result obtained by simultaneously injecting cyclosporin A and [γ-hydroxy-methylleucine⁴] cyclosporin A.

First, the cells were precultured for 4 days using an Erlenmeyer flask and then was inoculated in a fermentor. After 24 hours cyclosporin A dissolved in methanol was added to a final concentration of 100 mg/l. Cultures were harvested after 72 hours of inoculation. Ethylacetate was added to the culture, shaken and then separated. The organic solvent layer was evaporated to dryness, redissolved in methanol and then chromatographed on HPLC with a C-18 column, in which 100% of methanol 25% was flown for 2 minutes and decreased to 60% in 4 minutes, and then to 39% in 60 minute to elute the samples, with concomitant increase of acetonitrile. The liquid chromatography result showing cyclosporin A and biotransformed [γ-hydroxy-methylleucine⁴] cyclosporin A is represented in FIG. 1. The liquid chromatography results of purified [γ-hydroxy-methylleucine⁴] cyclosporin A and its simultaneous injection with cyclosporin A are represented in FIG. 2 and FIG. 3 respectively.

Example 2
Structural Determination of [γ-hydroxy-methylleucine⁴] cyclosporin A

Figure 4:
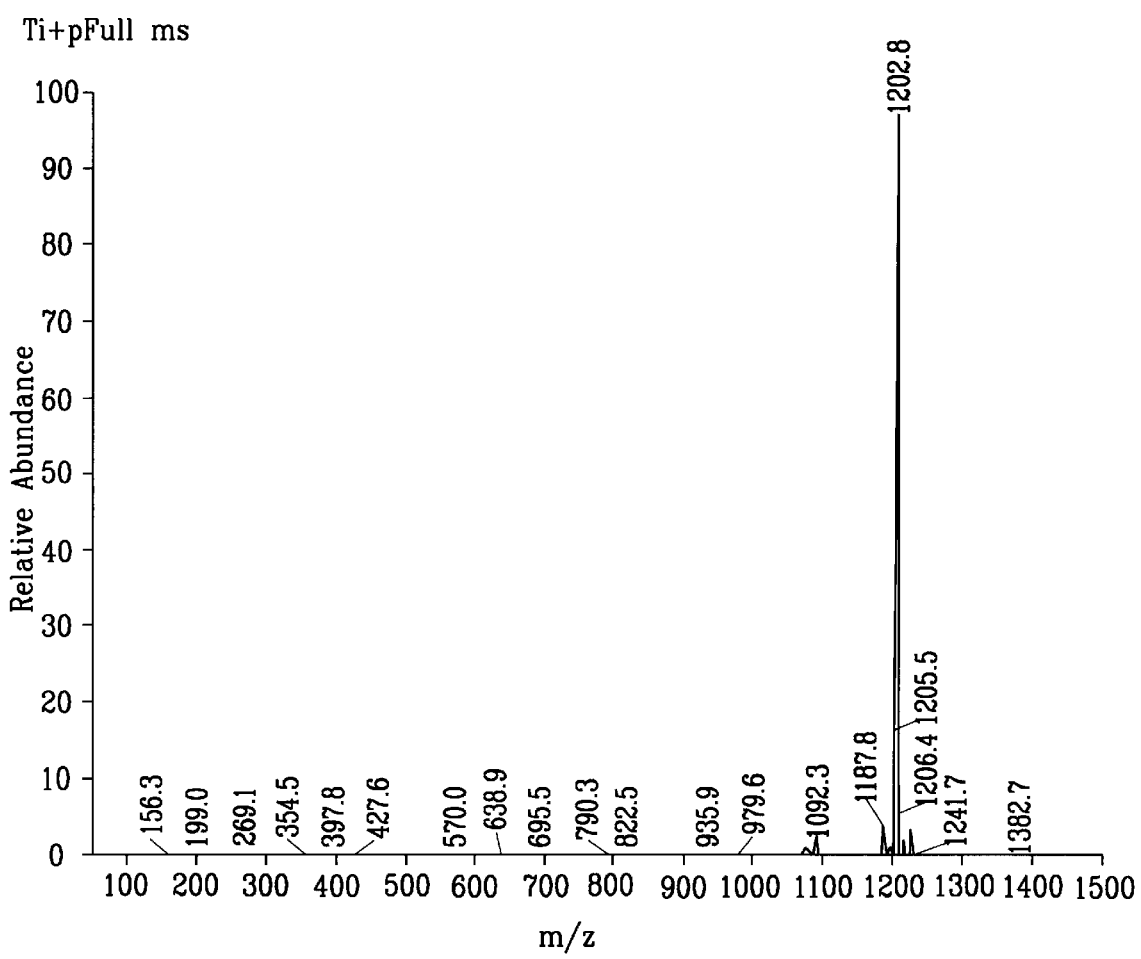
FIG. 4 is the LCQ Mass Spectrometer results for a cyclosporin A obtained by an Electro-Spray Ionization method, wherein [M(cyclosporin)+H] peak is at 1202.8 m/z.
Figure 5:
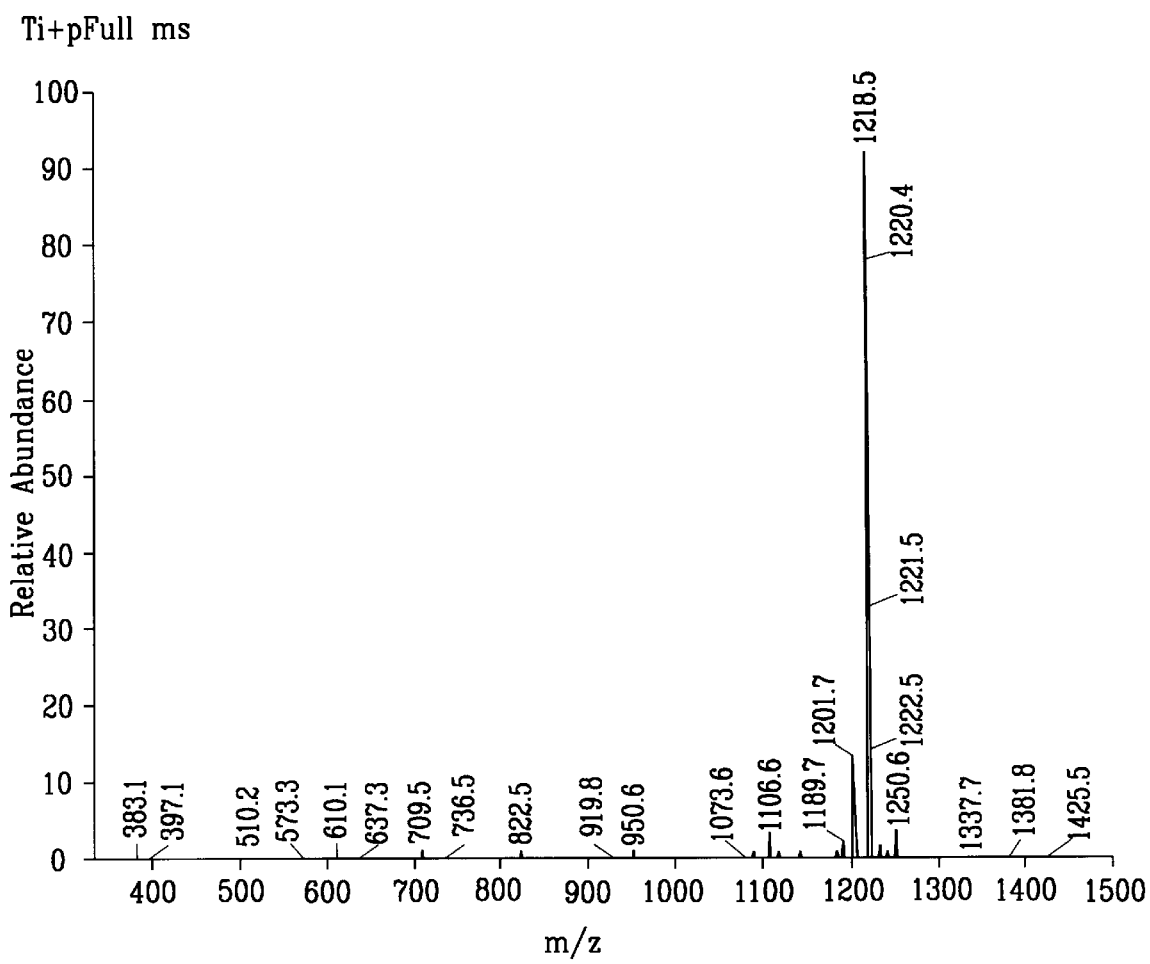
FIG. 5 is the LCQ Mass Spectrometer result for [γ-hydroxy-methylleucine⁴] cyclosporin A obtained by using an Electro-Spray Ionization method, wherein [M(cyclosporin derivative)+H] peak is at 1218.5 m/z in which the molecular weight is 16 higher than that of cyclosporin A.

A LCQ mass spectrophotometry (Finnigan, Calif.) using the ESI (electro-spray ionization) was used in order to analyze the structure of the [γ-hydroxy-methylleucine⁴] cyclosporin A. Cyclosporin A showed a [M(cyclosporin)+H] peak at 1202.8 m/z (FIG. 4), while [γ-hydroxy-methylleucine⁴] cyclosporin A showed a [M(cyclosporin derivatives)+H] peak at 1218.5 m/z, in which the molecular weight is 16 higher than that of cyclosporin A. Furthermore, the [M(cyclosporin)+Na] peak was detected at 1224.7 m/z in cyclosporin, and a [M(cyclosporin derivatives)+Na] peak was observed at 1240.7 m/z in the [γ-hydroxy-methylleucine⁴] cyclosporin A as the results of artificially adding sodium. From the above results, it could be presumed that a hydroxyl group was added (hydroxylation) to the cyclosporin molecules into [γ-hydroxy-methylleucine⁴] cyclosporin A.

Figure 6:
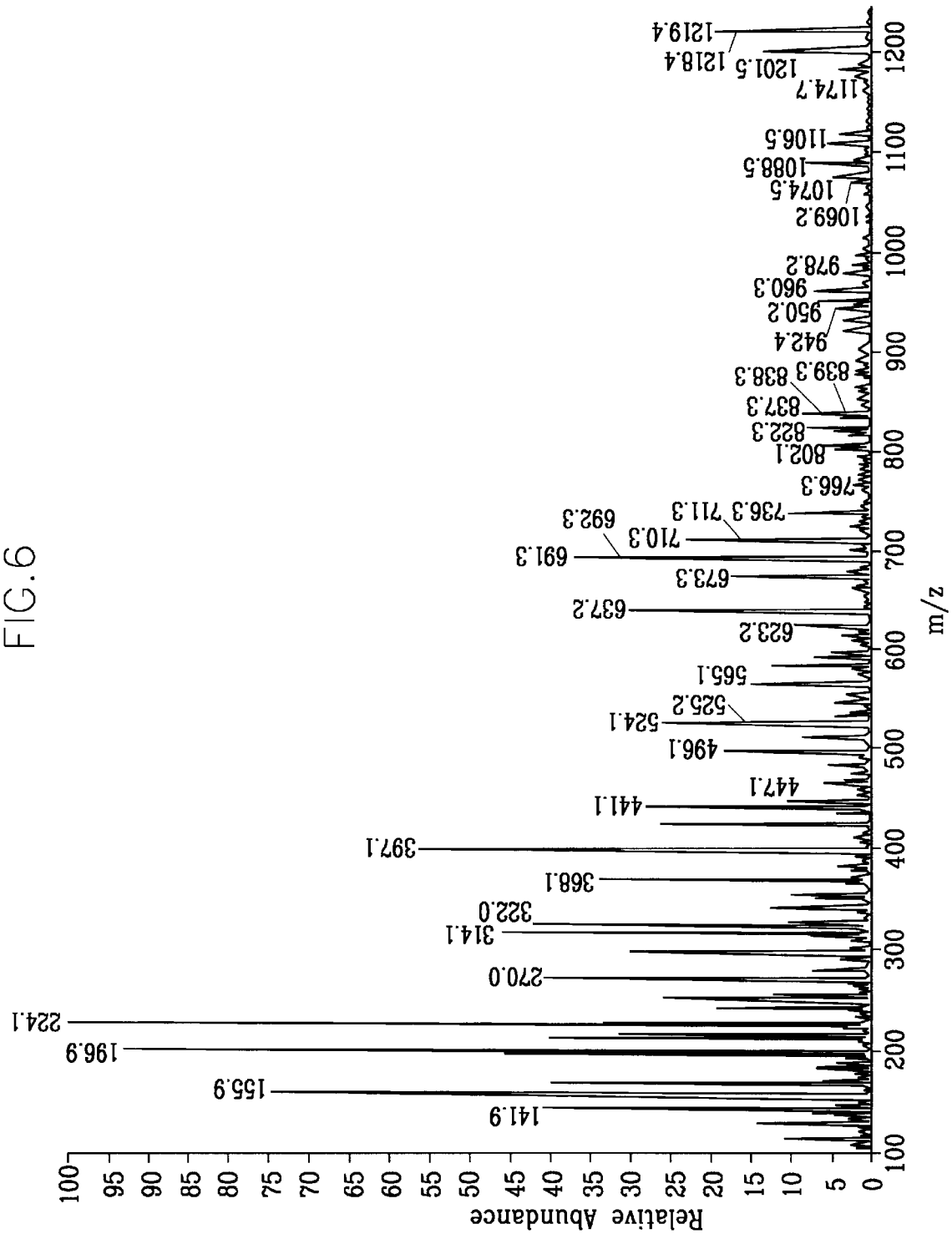
FIG. 6 is the Collision Induced Dissociation results for cyclosporin A.

The CID (collision induced dissociation) method was used in order to confirm the position of amino acids in which hydroxylation had occurred among 11 amino acids of cyclosporin. After forming fragment ions by the collision induced dissociation method, a fragment ion pattern formed from cyclosporin A (FIG. 6) and the [γ-hydroxy-methylleucine⁴] cyclosporin A was comparatively analyzed. When referring to fragment ion patterns of FIG. 7, it was found that there were no mass value changes in fragment ions of any other amino acids but in the peak comprising the No. 4 position amino acid in which the mass value of 16 was increased. Therefore, it could be known that the hydroxylation had occurred at the No. 4 position amino acid.

Figure 8:
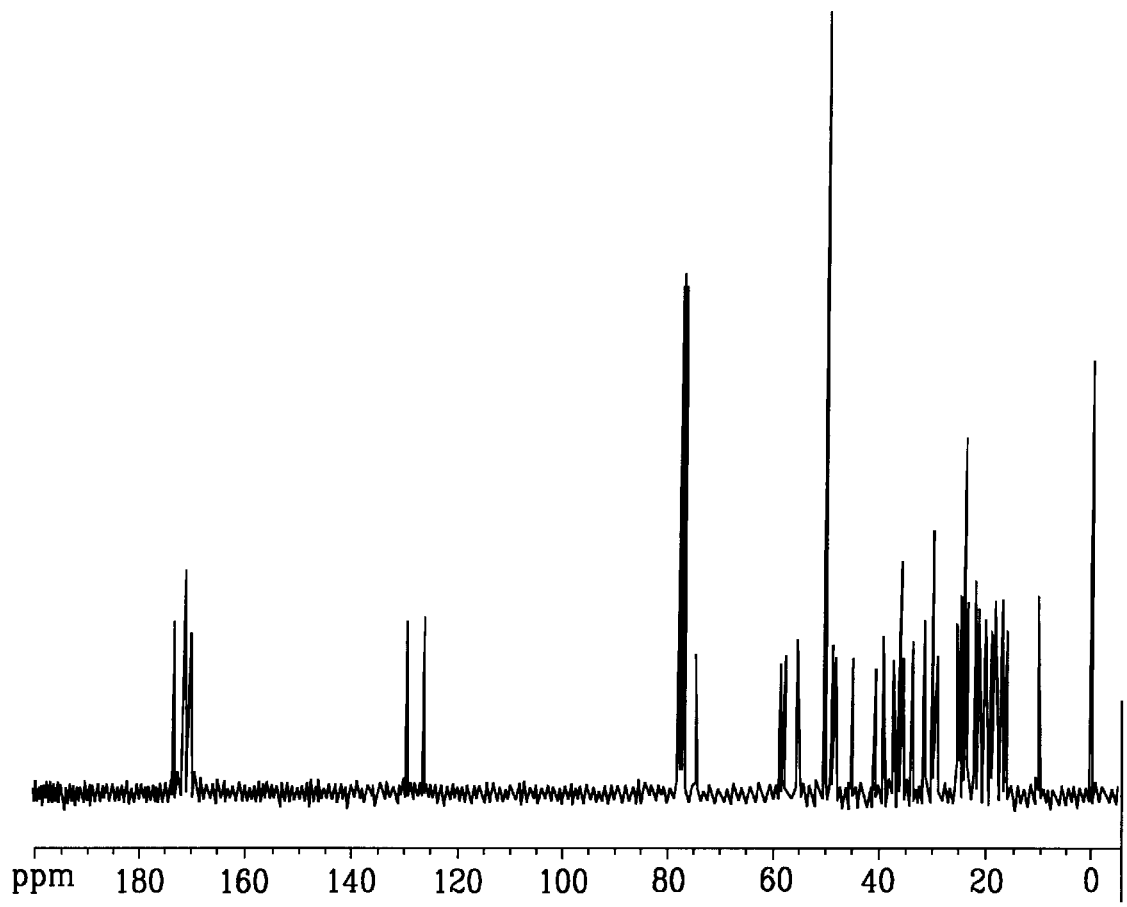
FIG. 8 is a $^{13}$C-Nuclear Magnetic Resonance spectrum of cyclosporin A.
Figure 9:
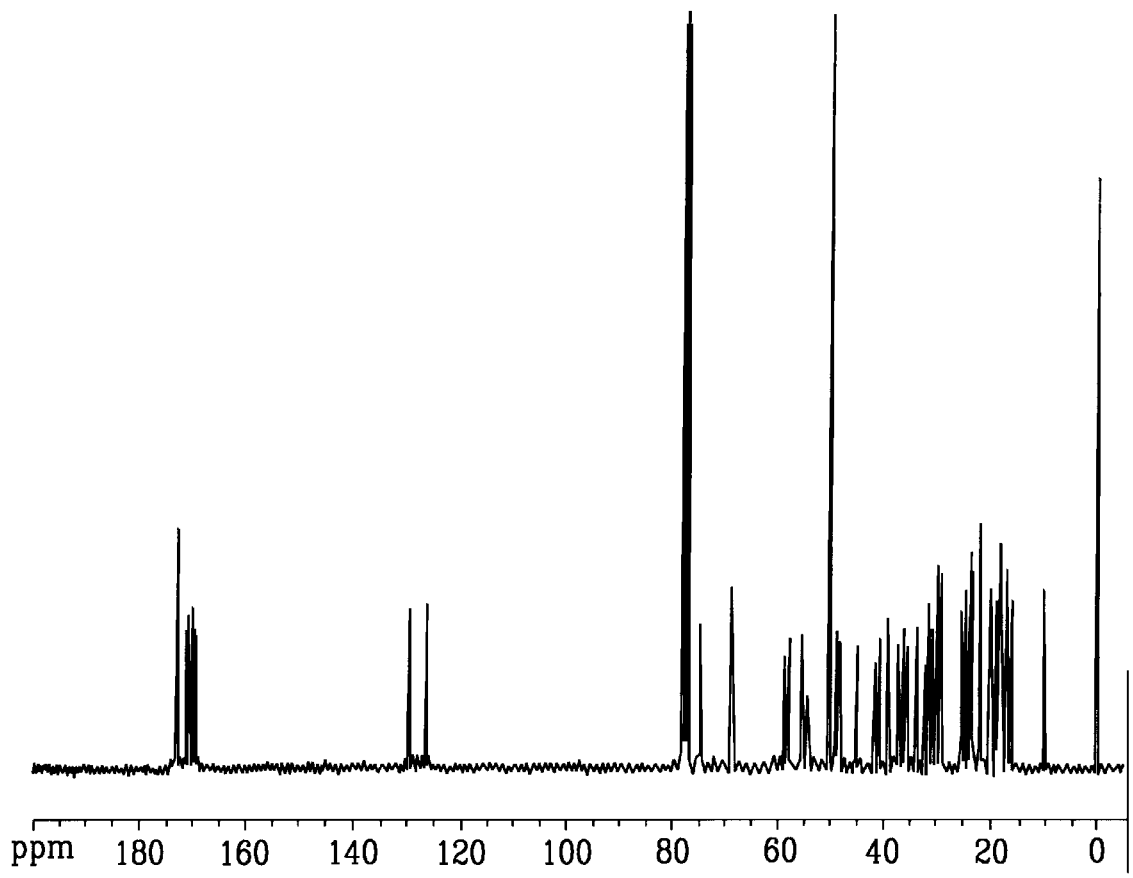
FIG. 9 is a $^{13}$C-Nuclear Magnetic Resonance spectrum of [γ-hydroxy-methylleucine⁴] cyclosporin A.

The nuclear magnetic resonance spectroscopy (ARX 300 MHz, Bruker, Germany) was additionally applied in order to confirm the position of the hydroxyl group added to the No. 4 amino acid. First, a new peak 69.00 ppm representing a chemical shift of carbon comprising added hydroxyl groups was found as a result of comparing ¹³C-Nuclear Magnetic Resonance spectrums of cyclosporin A (FIG. 8) and [γ-hydroxy-methylleucine⁴] cyclosporin A (FIG. 9).

Figure 10:
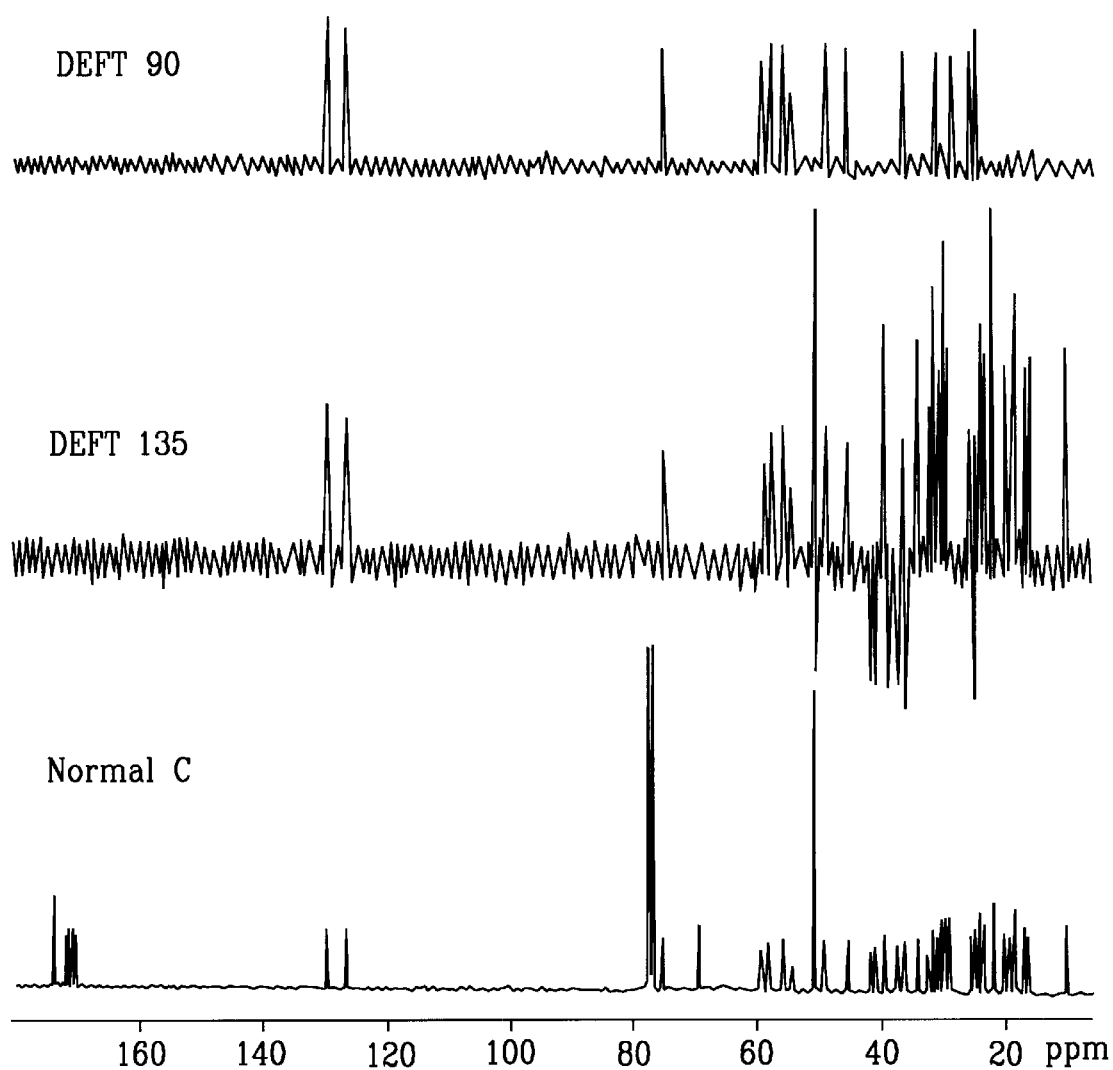
FIG. 10 is the DEPT (distortionless enhancement by polarization transfer) results for a new 69 ppm peak of a [γ-hydroxy-methylleucine⁴] cyclosporin A molecule, demonstrating the new carbon peak with hydroxyl group attached is a quaternary carbon.
Figure 11:
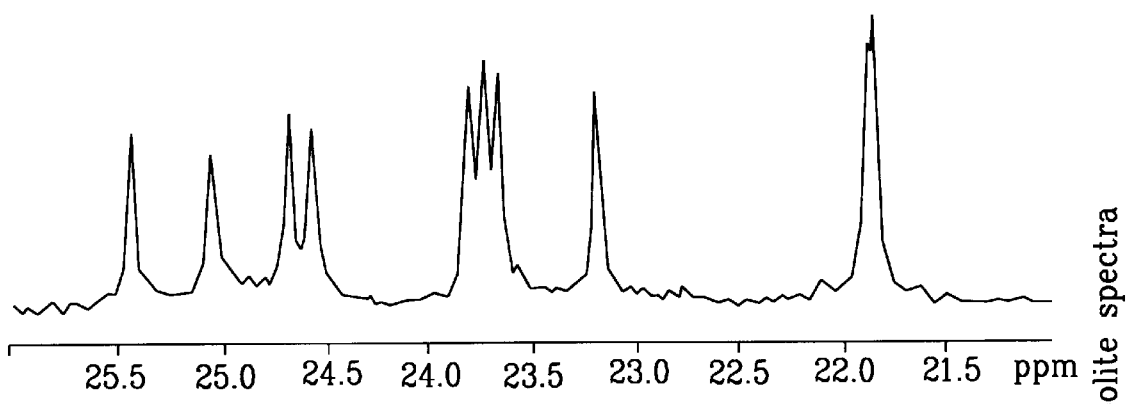
FIG. 11 illustrates a $^{13}$C-Nuclear Magnetic Resonance spectrum of cyclosporin A and [γ-hydroxy-methylleucine⁴] cyclosporin A, wherein a peak in the vicinity of 25 ppm has been removed by microorganisms.
Figure 11:
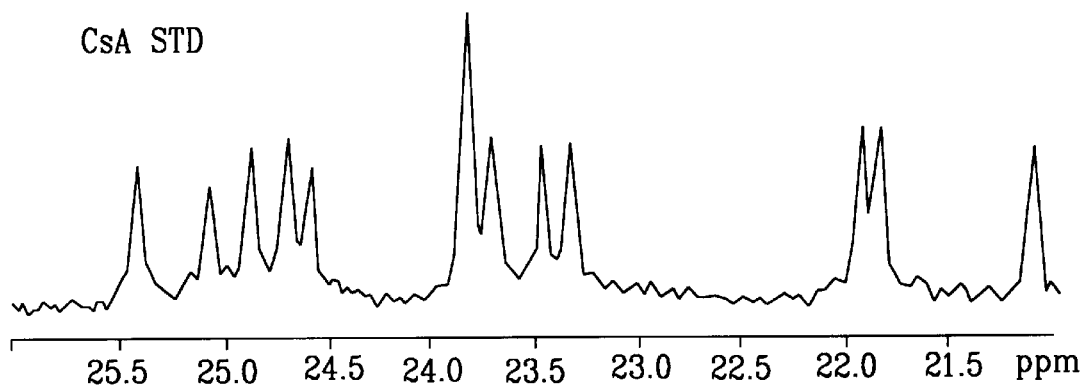

As the result of the DEPT (distortionless enhancement by polarization transfer) for the new peak at 69 ppm (FIG. 10), the carbon with hydroxyl group added was known to be quaternized, and this quaternization was confirmed to be made by the addition of a hydroxyl group to the carbon position of the No. 4 amino acids (hydroxylation). If quaternization had occurred with carbon of the No. 4 amino acid, the peak would have been shifted down field to the vicinity of 90 ppm. FIG. 11 shows that the peak disappeared by microorganisms is in the vicinity of 25 ppm, and it can be known from FIG. 12, 13 that the one disappeared would be one of 4 methine carbons on 4 methyl leucine in cyclosporin A molecules, as the DEPT results show.

Summing up, it could be known that a hydroxyl group was added to the carbon on No. 4 amino acid (methyl leucine) as the result of the mass spectroscopy using electron-spray ionization and collision induced dissociation, and the hydroxylation on the position carbon on No. 4 amino acid was confirmed by the nuclear magnetic resonance spectroscopy.

Example 3

Preparation of a Hair Revitalizing Tonic Containing [γ-hydroxy-methylleucine[4]] cyclosporin A A hair revitalizing tonic was prepared in 3 types represented in the following Table 1 by mixing, agitating, and completely dissolving each raw material.

TABLE 1

| Ingredients (wt %) | Preparation form 1 | Preparation form 2 | Preparation form 3 |
| --- | --- | --- | --- |
| Ethanol | 40.0 | 40.0 | 40.0 |
| [γ-hydroxy-methylleucine[4]] cyclosporin A | 0.1 | 1.0 | 8.0 |
| Tocopherol acetic acid | 0.1 | 0.1 | 0.1 |
| Salicylic acid | 0.3 | 0.3 | 0.3 |
| L-menthol | 0.3 | 0.3 | 0.3 |
| Tween 20 | 0.5 | 0.5 | 0.5 |
| Perfume | Appropriate amount | Appropriate amount | Appropriate amount |
| Colorant | Appropriate amount | Appropriate amount | Appropriate amount |
| Water | Balance | Balance | Balance |

Example 4

Preparation of a Hair Cream Containing [γ-hydroxy-methylleucine[4]] cyclosporin A Oil soluble ingredients and water soluble ingredients were completely dissolved in each phase by separately mixing and raw material at 80° C. in 3 types of preparation forms represented in the following Table 2. The two prepared phases heated to 80° were mixed and emulsified. After completing the emulsification and cooling to room temperature, a hair cream was prepared by adding and mixing perfume and colorant. An amount of water was added so that the total amount of two phases could be adjusted to 100 wt %.

TABLE 2

| Ingredients (wt %) | | Preparation form 1 | Preparation form 2 | Preparation form 3 |
| --- | --- | --- | --- | --- |
| Oil Phase | Paraffin | 5.0 | 5.0 | 5.0 |
| | Cetostearyl alcohol | 5.5 | 5.5 | 5.5 |
| | Petrolatum | 5.5 | 5.5 | 5.5 |
| | Glycerine monosterate | 3.0 | 3.0 | 3.0 |
| | Polyoxyethyleneoctyldodecylether | 3.0 | 3.0 | 3.0 |
| | Propylparaben | 0.3 | 0.3 | 0.3 |
| | [γ-hydroxy-methyl-leucine[4]] cyclosporin A | 0.1 | 1.0 | 8.0 |
| Water Phase | Glycerin | 7.0 | 7.0 | 7.0 |
| | Dipropylglycol | 20.0 | 20.0 | 20.0 |
| | Polyethylene glycol | 5.0 | 5.0 | 5.0 |
| | Water | 45.6 | 44.7 | 37.7 |
| Perfume | | Appropriate amount | Appropriate amount | Appropriate amount |

TABLE 2-continued

| Ingredients (wt %) | Preparation form 1 | Preparation form 2 | Preparation form 3 |
| --- | --- | --- | --- |
| Colorant | Appropriate amount | Appropriate amount | Appropriate amount |

Example 5

Preparation of a Shampoo Containing cyclosporin A Derivatives

After mixing the raw materials, except the perfume, pigment, and water in the 3 types of preparation forms represented in the following Table 3, the mixture was completely dissolved by heating as well as agitating. After cooling the mixture to room temperature and adding perfume and colorant to it, a shampoo was prepared by finally adding water so that the total composition content could be adjusted to 100 wt %.

TABLE 3

| Ingredient (wt %) | Preparation form 1 | Preparation form 2 | Preparation form 3 |
| --- | --- | --- | --- |
| Sodium POE laurylsulfuric acid (30 wt% aqueous solution) | 40.0 | 40.0 | 40.0 |
| Coconut oil fatty acid diethanolamide | 3.0 | 3.0 | 3.0 |
| 1, 2-propylene glycol | 2.0 | 2.0 | 2.0 |
| Methyl paraoxybenzoic acid | 0.2 | 0.2 | 0.2 |
| Ethanol | 2.0 | 2.0 | 2.0 |
| [γ-hydroxy-methyl-leucine[4]] cyclosporin A | 1.0 | 3.0 | 10.0 |
| Salicylic acid | 0.3 | 0.3 | 0.3 |
| L-menthol | 0.3 | 0.3 | 0.3 |
| Perfume | Appropriate amount | Appropriate amount | Appropriate amount |
| Colorant | Appropriate amount | Appropriate amount | Appropriate amount |
| Water | Balance | Balance | Balance |

Example 6

Preparation of Hair Conditioner Containing [γ-hydroxy-methylleucine[4]] cyclosporin A The oil soluble raw materials and water soluble raw materials were mixed separately in the 3 types of preparation forms represented in the following Table 4, and completely dissolved by heating to 80° C. The prepared oil phased raw materials and water phased raw materials at 80° were then mixed together and emulsified. After the emulsification and cooling to room temperature, a hair conditioner was prepared by adding and mixing perfume and pigment.

The amount of water was added so that the mixture could be adjusted to 100 weight %.

TABLE 4

| Ingredients (wt %) | | Preparation form 1 | Preparation form 2 | Preparation form 3 |
| --- | --- | --- | --- | --- |
| Oil phase | Cetanol | 3.0 | 3.0 | 3.0 |
| | Self-emulsion type glycerolmonostearate | 2.0 | 2.0 | 2.0 |
| | Squalene | 10.0 | 10.0 | 10.0 |

TABLE 4-continued

| Ingredients (wt %) | | Prep-aration form 1 | Prep-aration form 2 | Prep-aration form 3 |
|---|---|---|---|---|
| | [γ-hydroxy-methyl-leucine⁴] cyclosporin A | 1.0 | 5.0 | 10.0 |
| Water phase | Propyleneglycol | 2.0 | 2.0 | 2.0 |
| | Stearyldimethylbenzylammonium chloride (25 wt % aqueous solution) | 8.0 | 8.0 | 8.0 |
| | Methyl paraoxybenzoic acid | 0.2 | 0.2 | 0.2 |
| | Salicylic acid | 0.3 | 0.3 | 0.3 |
| | El-menthol | 0.3 | 0.3 | 0.3 |
| | Water | 73.2 | 69.2 | 64.2 |
| Perfume | | Appropriate amount | Appropriate amount | Appropriate amount |
| Colorant | | Appropriate amount | Appropriate amount | Appropriate amount |

Test Example 1

In vivo Hair Growth Promoting Effects of [γ-hydroxy-methylleucine⁴] cyclosporin A Seven week-old, female C57BL/6 mice were housed in groups of 7 to 11 animals. Mice were in the telogen stage of the hair cycle when used, as indicated by the pinkish color of the skin.

The mice's hair of the region of back was shaved by a clipper. After a one day for adaptation 100 ul of [γ-hydroxy-methylleucine⁴] cyclosporin A was applied on the shaved portion once a day for a period of 30 days. After determining the degree of hair growth by the naked eye, the results were photographed. As seen in FIG. 14 to FIG. 16, remarkable hair growth promoting effects existed when cyclosporin A and its derivative, [γ-hydroxy-methyl-leucine⁴] cyclosporin A of EXAMPLE 1 were applied, compared to the control group on which only a vehicle was applied. It was found that the difference between cyclosporin A and its derivative of [γ-hydroxy-methyl-leucine⁴] cyclosporin A of EXAMPLE 1 was inappreciable. In contrast, animals treated with the derivatives (the 11 derivatives mentioned in REFERENCE EXAMPLES 6 to 11) were almost at the level of the control group, having virtually no effects (data not shown).

The test expanded to the derivatives modified on No. 4 amino acid, methylleucine. The results of the hair growth-stimulating effects on the derivatives in which the original No. 4 amino acid, methylleucine, is substituted with the similarly structured methylisoleucine, methylvaline, leucine, isoleucine, methylalanine (REFERENCE EXAMPLES 1 to 5) are represented in FIG. 17 to FIG. 23, wherein the hair growth-stimulating effects of [methylleucine⁴] (FIG. 19), [methylvaline⁴] (FIG. 20), [leucine⁴] (FIG. 21), [isoleucine⁴] (FIG. 22), [methylalanine⁴] (FIG. 23) are shown to be much lesser than cyclosporin A (FIGS. 18, 16) and [hydroxy-methyl-leucine] cyclosporin A (FIG. 15).

That is, as a result of comparing the trichological evaluations of various types of cyclosporin A derivatives, it was observed that only [γ-hydroxy-methyl-leucine⁴] cyclosporin A showed the similar effects to cyclopsorin A.

Any appreciable skin irritation was not found in the control group or in any of the treated group s during the 30 days of the experiment.

Test Example 2

Immunosuppressive Test of cyclosporin A Derivatives

The mouse mixed lymphocyte reaction (MLR), by mixing two different types of mouse spleen cells and measuring the incorporation of labeled ³H-thymidine into DNA (J. Antibiotics, 1994; 47; 208–215) was used in the immunosuppressive activity.

After mixing equivalent numbers of BALB/c mouse spleen cells as the reacting cells and mitomycin treated C57BL/6 mouse spleen cells as the stimulating cells, the mixture was treated with various concentrations of cyclosporin A and [γ-hydroxy-methylleucine⁴] cyclosporin A. Then, the mixture was cultured in an RPMI medium containing mercaptoethanol and a 10% fetal bovine serum. After culturing for 4 days, it was additionally cultured for 4 hours after adding ³H-thymidine to it, and the $IC_{50}$(ug/ml) each compound for the immunosuppresion was calculated by measuring the influx of labeled ³H-thymidine into DNA using a liquid scintillation counter.

As a result, the $IC_{50}$(ug/ml) of [γ-hydroxy-methyl-leucine⁴] cyclosporin A was shown to be 5.3, 6.8, and 5.3, which represents a greater than 100-fold decrease in immunosuppressive activity compared to cyclosporin A in which the $IC_{50}$ was 0.034, 0.05, and 0.031. This is a similar level to that shown in the literatures (J. Antibiotics, 1996, 49, 781–787, and J. Virol., 1995; 69; 2451–2461).

That is, it was found that [γ-hydroxy-methyl-leucine⁴] cyclosporin A in which a hydroxyl group is added to the carbon position of cyclosporin No. 4 methylleucine by the microorganism not only have a much lower degree of immunosuppressive activity, but as the previous data show, also maintains superior hair growth effects as compared to cyclosporin A.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A method for treating alopecia and promoting hair growth which comprises treating a patient in need thereof with a pharmaceutical non-immunosuppressive composition containing [γ-hydroxy-methylleucine⁴] cyclosporin A represented in the following formula as an active component and suitable carriers:

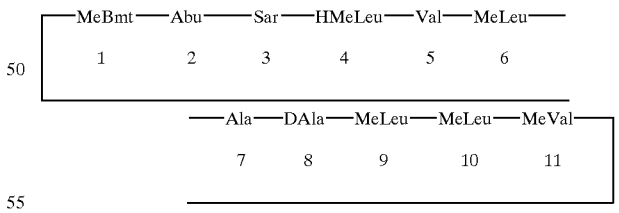

where MeBmt is N-methyl-(4R)-4-[(E)-2-butenyl]-4-methyl-L-threonine, Abu is L-aminobutyric acid, Sar is Sarcosine, HMeLeu is γ-hydroxy-methylleucine, Val is L-valine, MeLeu is N-methyl-L-leucine, Ala is L-alanine, DAla is D-alanine, and MeVal is N-methyl-L-Valine.

2. The method of claim 1 wherein said composition is prepared in one or more forms selected from the group consisting of a liquid phase, spray, gel, paste, emulsion, cream, and shampoo.

* * * * *

UNITED STATES PATENT AND TRADEMARK OFFICE
CERTIFICATE OF CORRECTION

PATENT NO. : 6,521,595 B1
DATED : February 18, 2003
INVENTOR(S) : Kim et al.

It is certified that error appears in the above-identified patent and that said Letters Patent is hereby corrected as shown below:

<u>Title page,</u>
Item [57], ABSTRACT,
Line 6, before "carbon" insert -- γ --.

<u>Column 7,</u>
Line 37, in the formula, "MeLeu" should read -- MeLeu$^9$ --.

<u>Column 8,</u>
Line 52, "69.00ppm" should read -- (δ 69.00 ppm) --;
Line 61, "carbon" should read -- γ-carbon --;
Line 63, "carbon" should read -- α-carbon --.

<u>Column 9,</u>
Line 4, "carbon" should read -- γ carbon --;
Line 7, "position" should read -- γ position --;
Line 41, "3" should read -- three --;
Line 43, after "80°" insert -- C. --.

<u>Column 10,</u>
Line 52, after "80°" insert -- C. --.

<u>Column 11,</u>
Line 31, "100 ul" should read -- 100 $\mu\ell$ (0.1% w/v) --;
Line 59, before "hydroxy" insert -- γ --.

UNITED STATES PATENT AND TRADEMARK OFFICE
CERTIFICATE OF CORRECTION

PATENT NO. : 6,521,595 B1
DATED : February 18, 2003
INVENTOR(S) : Kim et al.

It is certified that error appears in the above-identified patent and that said Letters Patent is hereby corrected as shown below:

<u>Column 12,</u>
Line 17, before "each" insert -- of --;
Line 29, "carbon" should read -- γ-carbon --;

Line 58, "Abu is L-aminobutyric acid" should read -- Abu is L- α aminobutyric acid --;
Line 65, after "cream," insert -- conditioner, --.

Signed and Sealed this

Twenty-second Day of July, 2003

JAMES E. ROGAN
*Director of the United States Patent and Trademark Office*